United States Patent [19]

Foley et al.

[11] Patent Number: 4,591,578

[45] Date of Patent: May 27, 1986

[54] CATALYST OF MOLYBDENUM ON WIDE-PORE CARBON SUPPORT

[75] Inventors: Henry C. Foley, East Norwalk; Michael P. O'Toole, Stamford, both of Conn.

[73] Assignee: American Cyanamid Company, Stamford, Conn.

[21] Appl. No.: 698,060

[22] Filed: Feb. 4, 1985

[51] Int. Cl.$^4$ .................. B01J 21/18; B01J 23/28; B01J 23/64

[52] U.S. Cl. .................. 502/185; 502/182; 518/714

[58] Field of Search .................. 502/182, 185, 321; 518/714

[56] References Cited

U.S. PATENT DOCUMENTS 4,151,190 4/1979 Murchison et al. ............ 502/185 X
4,413,063 11/1983 Audibert et al. ............... 518/714 X

*Primary Examiner*—W. J. Shine
*Attorney, Agent, or Firm*—Gordon L. Hart

[57] ABSTRACT

New catalysts comprising molybdenum on supports of defined wide-pore carbons are useful as catalyst for reaction of CO with $H_2$ for synthesis of hydrocarbons. Catalysts may be made by depositing $Mo(CO)_6$ on the carbon support particles by vapor deposition or solution impregnation. The catalyst may also comprise a second metal, such as rhodium or palladium.

4 Claims, No Drawings

CATALYST OF MOLYBDENUM ON WIDE-PORE CARBON SUPPORT

The invention relates to improvements in catalysts for the catalytic reaction of hydrogen and carbon monoxide to produce methane and other aliphatic hydrocarbons. More particularly the invention provides improved catalysts for such reaction, comprising catalytic molybdenum on wide-pore carbon.

Wide-pore carbons are particulate carbons having pore size distribution curves characterized by a single, sharp peak at a pore radius above 10 Å, usually in the range from about 10 to about 100 angstroms, and having surface area greater than 100 square meters per gram ($m^2/g$), usually in the range from about 300 to about 700 $m^2/g$, and having pore volume greater than 0.2 cc/g. Average pore radius is a calculated function of the pore volume and the surface area, expressed by the formula:

$$r = 2PV/SA \times 10^4$$

where:
  r = average pore radius, Å.
  PV = pore volume, cc/g
  SA = surface area (BET), $m^2/g$.

Wide-pore carbons are characterized by average pore radius of at least 25 angstrom units, and usually have compacted bulk density in the range from about 0.3 to about 0.8 g/cc.

Wide-pore carbons, their properties and methods for their preparation were described in U.S. Pat. Nos. 4,035,260, 4,029,600, 4,081,370, 4,031,137 and 3,978,000. Those carbons were prepared by dispersing carbon black in a resin binder, preferably poly(furfuryl alcohol), forming particles of the mixture and then carbonizing the binder to produce wide-pore carbon particles having the properties defined above. Catalysts comprising platinum group metals on wide-pore carbon and their use for hydrogen reduction of dinitrotoluene, were described in U.S. Pat. No. 4,031,137.

The catalysts of the present invention are made on wide-pore carbon of the kind described, but differ from catalysts described in the above patents both by the catalytic metals that are used and by the catalytic reactions for which the catalysts are designed.

Molybdenum is the principal catalytic metal in catalysts according to the present invention, and the catalysts comprising molybdenum on wide-pore carbon are designed as catalysts for reaction of hydrogen and carbon monoxide by the Fischer-Tropsch synthesis. The catalytic reaction produces hydrocarbons, mostly methane but also other alkanes and alkenes having two or more carbon atoms.

We have found that catalysts comprising molybdenum on wide-pore carbon have improved activity for catalysis of the reaction of hydrogen and carbon monoxide, as compared with molybdenum on ordinary carbon supports or on alumina supports. The activity of molybdenum on wide-pore carbon can be improved further by certain preferred methods of impregnating the metal on the carbon support. Furthermore, catalysts having better catalytic activity at reduced reaction temperatures are made by combining molybdenum and a second catalytic or promoter metal, preferably a platinum group metal on the wide-pore carbon support.

Catalysts comprising molybdenum on wide-pore carbon can be made by saturating the porous wide-pore carbon support with a liquid solution of molybdenum compound in an organic or aqueous solvent, followed by evaporation of the solvent. Preferably the molybdenum can be deposited on surfaces of the carbon support by vapor deposition of a volatile molybdenum compound such as $Mo(CO)_6$. The molybdenum compound which has been deposited on the carbon surface by solution impregnation or by vapor deposition is decomposed or reduced to the metal or metal oxide by calcining at a temperature high enough to cause the decomposition or reduction.

We have found that catalytic activity of carbon supported molybdenum catalysts for the hydrogenation reaction will be determined at least in part by the method of making the catalyst. Catalysts made by vapor deposition of molybdenum hexacarbonyl on wide-pore carbon supports are found to have outstanding catalytic activity for hydrogenation of CO.

Following are examples illustrating some preferred catalysts according to the invention and how they can be made and used in catalytic hydrogenation of CO to make hydrocarbons.

EXAMPLE 1

The wide-pore carbon (WPC) selected as a support has been prepared from carbon black and poly(furfuryl alcohol) according to the method described in U.S. patents cited above. The WPC support particles have surface area of 450 $m^2/g$, pore volume 0.85 cc/g and average pore radius of 37.8 Å. One gram (1.0044 g) of this WPC is heated in air at 120° C. for five days. The carbon is then physically mixed with 0.5074 g of $Mo(CO)_6$. The mixture is placed in a Carius tube which is then evacuated and immersed in an oil bath held at 190° C. for 48 hours. Upon cooling the tube to room temperature, 0.1459 g of $Mo(CO)_6$ is found to have crystallized in the tip of the Carius tube. The solid catalyst recovered weighs 1.1655 g. The $Mo(CO)_6$ has been vaporized and part of it has sublimed on the surface area of the carbon. Molybdenum content of the catalyst measured by EDX is 10.7% actual wt. percent Mo. The composition of the molybdenum carbonyl on the carbon has changed indicating some reduced valence of the molybdenum due to heating in the presence of reducing agents.

The carbon-supported catalyst particles are sieved to 40×80 mesh and a 0.5 cc sample of the 40×80 mesh material is weighed and loaded into a tubular reactor between plugs of glass wool. In the reactor the catalyst bed is pretreated by flowing nitrogen or hydrogen through the bed at the pretreatment temperature and for the time shown in Table I. Following the pretreatment, a 1:1 volume mixture of $CO:H_2$ is flowed through the bed at the test temperature and pressure shown in Table I and at gas hourly space velocity of 2400 $Hr.^{-1}$. The product stream is analyzed for conversion to hydrocarbons by online analysis using a gas chromatograph equipped with a 12 ft. Poropac S column and a flame ionization detector. From the results of the analysis, the percent CO converted to hydrocarbons and the rate of formation of $C_1$–$C_6$ hydrocarbons were calculated. In Table I, the percent conversion of CO to hydrocarbons and the rate of formation for methane are shown. The rate of formation of methane will be the more significant measure of activity for comparison of different catalysts tested as it indicates a relative activity for the catalyst on the basis of catalyst metal weight, regardless of the metal loading. The percent conversion figures and the rate figures in Table I are small because the tests were operated at pressures much below the pressures that would usually be used for a production reactor. Several samples of the same catalyst are pretreated and tested as described, with variation of specific conditions and varying results as shown in Table I.

Molybdenum can be deposited on wide-pore carbon by solution impregnation using aqueous solutions of a water soluble molybdenum compound that can be decomposed to the metal oxide or reduced to the metal by heating. Ammonium heptamolybdate $(NH_4)_6Mo_7O_{24}$ is a preferred compound of molybdenum for this use.

EXAMPLE 2

A solution of 23 g of $(NH_4)_6Mo_7O_{24}$ in 30 ml water was prepared and divided into five aliquots. A 50 g sample of wide-pore carbon pellets was impregnated with one 6 ml aliquot of the solution and then dried by heating in air at 125° C. for 15 hours. This was repeated with each aliquot until all of the molybdate was deposited on the carbon. The sample was then heated in air at 250° C. for one hour. The weight percent loading of Mo on the finished catalyst was 20% by wt Mo on carbon. For comparison, a support of gamma-alumina was impregnated in the same manner to make a catalyst of 20% by wt Mo on alumina. The carbon and alumina catalysts were both tested by the test method described in Example 1. Conditions for catalyst pretreatment, test conditions and test results are tabulated in Table I. The molybdenum catalyst on the wide-pore carbon support was significantly more active than a catalyst prepared by the same method on the alumina support.

EXAMPLE 3

Molybdenum hexacarbonyl $Mo(CO)_6$ can be impregnated on wide-pore carbon by solution impregnation using an organic solvent, such as acetone, tetrahydrofuran (THF), methylene chloride or ether, in which the molybdenum hexacarbonyl is soluble. Two grams of wide-pore carbon in 100 ml of THF was refluxed for twenty minutes under nitrogen. One gram of $Mo(CO)_6$ was added and the reflux was continued for 6 hours. After cooling, the green supernatant liquid was flash evaporated and the solid carbon material was dried in air at 120° C. for 13 hrs. The catalyst contained 16.4 wt percent Mo. This catalyst was tested for activity by the test described at Example 1, using the pretreatment temperatures and times, test temperatures and pressure as tabulated in Table I, which also shows the test results.

Molybdenum when used in combination with lesser proportions of a metal selected from the group consisting of Pt, Rh and Cu on carbon supports, as catalyst for reaction of hydrogen with carbon monoxide, is found to have significant catalytic activity under conditions of temperature and pressure less severe than those needed when using molybdenum without the second metal. The product yields using the metals in combination are more than the additive yields from using each metal separately. Also, as compared with yields obtained using either metal alone, the $C_2$ to $C_5$ hydrocarbon products were found to contain higher proportions of olefin components, most notably when operating at lower temperatures in the temperature range tested.

TABLE I

Molybdenum/WPC

| | Catalyst Pretreatment | | | Test Pressure Psig | % CO Conv. to Hydrocarbons | Rates of hydrocarbon formation micromoles per sec per gm of Mo | | | | | |
|---|---|---|---|---|---|---|---|---|---|---|---|
| | Gas | Temp °C. | Time Min | Test Temp °C. | | | $C_1$ | $C_2$ | $C_3$ | $C_4$ | $C_5$ | $C_6$ |
| Example 1 | $N_2$ | 300 | 120 | 350 | 0 | 0.6 | .64 | .23 | 0.08 | .01 | — | — |
| $Mo(CO)_6$ | $N_2$ | 400 | 20 | 400 | 0 | 4.5 | 6.50 | 1.56 | 0.22 | .04 | — | — |
| on WPC | $H_2$ | 400 | 20 | 400 | 0 | 4.4 | 4.76 | 2.11 | 0.37 | .05 | — | — |
| by Vapor | $H_2$ | 400 | 20 | 350 | 45 | 7.0 | 377.9 | 123.57 | 27.3 | 9.61 | 0.164 | .09 |
| Deposition | $H_2$ | 400 | 20 | 400 | 45 | 16.7 | 1700.0 | 140.9 | 20.42 | 4.4 | 0.65 | .49 |
| Example 2 | $H_2$ | 450 | 60 | 300 | 45 | 2.3 | 45.8 | 11.5 | 3.3 | .81 | .26 | .05 |
| $(NH_4)_6$ | $H_2$ | 450 | 60 | 350 | 45 | 7.7 | 143.5 | 46.1 | 11.0 | 2.04 | .96 | .67 |
| $Mo_7O_{24}$ on Carbon by aqueous solution | | | | | | | | | | | | |
| $(NH_4)_6$ | $H_2$ | 450 | 60 | 300 | 45 | .08 | 13.2 | 22 | .46 | .22 | .36 | .18 |
| $Mo_7O_{24}$ | $H_2$ | 450 | 60 | 350 | 45 | 3.3 | 61.1 | 12.06 | 2.9 | .69 | .26 | .10 |
| on gamma alumina by aqueous solution | | | | | | | | | | | | |
| Example 3 | $H_2$ | 350 | 20 | 350 | 0 | 0.9 | .75 | 0.24 | .05 | — | — | — |
| $Mo(CO)_6$ | $H_2$ | 400 | 20 | 350 | 0 | 1.1 | 1.02 | 0.30 | .05 | — | — | — |
| on WPC | $H_2$ | 400 | 20 | 400 | 0 | 1.7 | 1.79 | 0.38 | .05 | — | — | — |
| by organic | $H_2$ | 450 | 20 | 350 | 0 | 1.0 | .96 | 0.27 | .04 | — | — | — |
| solution | $H_2$ | 450 | 20 | 400 | 0 | 2.8 | 2.93 | 0.62 | .07 | — | — | — |

EXAMPLE 4

Wide-pore carbon particles were prepared by carbonizing extruded particles of mixed carbon black and poly(furfuryl alcohol) by the procedure described in Example 3 of U.S. Pat. No. 4,031,137. The carbon particles were then impregnated with a solution of rhodium chloride, which was then reduced in hydrogen to deposit rhodium metal on the surface area of the carbon. The solution contained rhodium chloride in an amount to deposit 6% rhodium by wt on the carbon. The preparation of the catalyst is described in more detail in Example 8 of U.S. Pat. No. 4,031,137.

EXAMPLE 5

A wide-pore carbon:palladium catalyst was prepared by impregnating wide-pore carbon described in Example 4 with an aqueous acid solution of $PdCl_2$ then precipitating Pd on the carbon by raising the pH of the solution. A finished catalyst of 6% by wt Pd on carbon was obtained. The preparation is described in more detail in Example 10 of U.S. Pat. No. 4,031,137.

EXAMPLE 6

Samples of catalysts prepared in Examples 4 and 5 were further impregnated with molybdenum as follows. The catalyst samples were dried overnight at 120° C. in air. Two grams of each catalyst separately was thoroughly mixed with 1.1 g $Mo(CO)_6$ dissolved in 100 ml hexane, then the hexane was evaporated in vacuum. The dry catalyst, nominally 20% Mo+6% Pd or Rh on WPC, was heated in air at 120° C.

EXAMPLE 7

Catalysts prepared in Examples 4 and 5 were charged to reactors and pretreated in nitrogen for one hour at 400° C., and used as catalysts by the test method described in Example 1. Test conditions and test results are tabulated in Tables 3 and 5.

EXAMPLE 8

Samples of the catalysts prepared in Example 7 were charged to reactors and pretreated in nitrogen for one hour at 400° C., then used as catalysts by the test method described in Example 1. Test conditions and test results are tabulated in Tables 2 and 4 for the respective catalysts.

TABLE 2

Mo/Rh on WPC
Activity (Rate of formation-micromoles per sec per gm metal)
Catalyst 20% Mo + 6% Rh on WPC
(Press. 1 atm; $CO:H_2::1:1$, GHSV 2400)

| | Temp. °C. | | | |
|---|---|---|---|---|
| | 270° C. | 300° C. | 350° C. | 400° C. |
| Hydrocarbon Product Components | | | | |
| $C_1$ | 3.15 | 6.96 | 7.09 | 5.47 |
| $C_2^=$ | .01 | .01 | .01 | .02 |
| $C_2$ | .40 | .80 | .71 | .36 |
| $C_3^=$ | .04 | .00 | — | .01 |
| $C_3$ | .16 | .30 | .17 | .04 |
| $C_4$ iso | .00 | .00 | .00 | |
| $C_4^=$ | .00 | .00 | .00 | .00 |
| $C_4$ | .04 | .06 | .02 | .01 |
| $C_5^=$ | — | .00 | .00 | .00 |
| $C_5$ | .02 | .01 | .01 | |
| $C_6$ | .01 | .01 | .00 | |
| % CO Conversion | 4.6 | 9.3 | 8.7 | 6.1 |
| $C_2^=/C_2$ | 0.3 | .01 | .02 | .04 |
| $C_3^=/C_3$ | .23 | .00 | .00 | .27 |
| $C_2-C_6/C_1$ | .21 | .17 | .13 | .09 |

TABLE 3

Rh on WPC
Activity (Rate of formation-micromoles per sec per gm metal)
Catalyst 6% Rh on WPC
(Press. 1 atm; $CO:H_2::1:1$, GHSV 2400)

| | Temp. °C. | | |
|---|---|---|---|
| | 270° C. | 300° C. | 400° C. |
| Hydrocarbon Product Components | | | |
| $C_1$ | 1.20 | 3.24 | 10.85 |
| $C_2^=$ | .00 | .00 | .00 |
| $C_2$ | .00 | .15 | .18 |
| $C_3^=$ | .02 | — | — |
| $C_3$ | .04 | .08 | .02 |
| $C_4$ | .02 | .02 | .00 |

TABLE 3-continued

Rh on WPC
Activity (Rate of formation-micromoles per sec per gm metal)
Catalyst 6% Rh on WPC
(Press. 1 atm; $CO:H_2::1:1$, GHSV 2400)

| | Temp. °C. | | |
|---|---|---|---|
| | 270° C. | 300° C. | 400° C. |
| $C_5$ | .01 | .01 | — |
| $C_6$ | — | .01 | — |
| % CO Conversion | 0.4 | 1.0 | — |
| $C_2^=/C_2$ | .02 | .00 | — |
| $C_3^=/C_3$ | .35 | .00 | — |
| $C_2-C_6/C_1$ | .14 | .08 | — |

TABLE 4

Mo/Pd on WPC
Activity (Rate of formation-micromoles per sec per gm metal)
Catalyst 20% Mo + 6% Pd on WPC
(Press. 1 atm, $CO:H_2::1:1$, GHSV 2400)

| | Temp. °C. | | | |
|---|---|---|---|---|
| | 270° C. | 300° C. | 350° C. | 400° C. |
| Hydrocarbon Product Components | | | | |
| $C_1$ | .59 | 1.00 | 2.20 | 4.08 |
| $C_2^=$ | .02 | .01 | .01 | .01 |
| $C_2$ | .05 | .10 | .26 | .64 |
| $C_3^=$ | .02 | .01 | .00 | — |
| $C_3$ | .02 | .02 | .06 | .10 |
| $C_4$ Iso | .01 | .00 | .00 | .00 |
| $C_4^=$ | .00 | — | .00 | .00 |
| $C_4$ | .00 | .00 | .01 | .01 |
| $C_5^=$ | .00 | .00 | .00 | .00 |
| $C_5$ | — | .00 | — | .00 |
| % CO Conversion | .09 | 1.3 | 2.8 | 5.4 |
| $C_2^=/C_2$ | .39 | .12 | .04 | .02 |
| $C_3^=/C_3$ | 1.09 | .45 | .00 | .00 |
| $C_2-C_6/C_1$ | .22 | .16 | .15 | .19 |

TABLE 5

Pd on WPC
Activity (Rate of formation-micromoles per sec per gm metal)
Catalyst 6% Pd on WPC
(Press. 1 atm, $CO:H_2::1:1$, GHSV 2400)

| | Temp. °C. | | |
|---|---|---|---|
| | 270° C. | 300° C. | 400° C. |
| Hydrocarbon Product Components | | | |
| $C_1$ | .32 | .33 | .95 |
| $C_2^=$ | .04 | .04 | .04 |
| $C_2$ | .02 | .02 | .04 |
| $C_3^=$ | .03 | .03 | .05 |
| $C_4^=$ | .01 | .01 | .01 |
| $C_5^=$ | — | .00 | .00 |
| % CO Conversion | .2 | .2 | .4 |
| $C_2^=/C_2$ | 2.78 | 2.69 | 1.00 |
| $C_2-C_6C_1$ | .32 | .29 | .16 |

Results in Tables 2–4 show the bimetallic Mo-Rh and Mo-Pd on the wide-pore carbon supports had higher activities than a catalyst made with either of the catalytic metals alone on the same support. The Rh-Mo catalyst showed higher activity than the Pd-Mo catalyst but the olefin/paraffin ratio was higher with the latter.

EXAMPLE 9

Samples of the catalysts prepared in Example 7 were charged to reactors and pretreated as in Example 8 but were tested as in Example 1, except at higher operating pressure, lower temperature and slower gas hourly space velocity (GHSV). The test conditions and results are tabulated in Tables 6 and 7.

TABLE 6

Mo/Rh on WPC
Activity (Rate of formation-micromoles per sec per gm metal)
Catalyst 20% Mo + 6% Rh on WPC
(Press. = 4 atm; CO:$H_2$::1:1; GHSV = 336)

| | Temp. °C. |
| --- | --- |
| | 200° C. |
| Hydrocarbon Product Components | |
| $C_1$ | 1.87 |
| $C_2=$ | 0.4 |
| $C_2$ | .14 |
| $C_3=$ | .06 |
| $C_3$ | .03 |
| $C_4$ iso | .01 |
| $C_4=$ | .02 |
| $C_4$ | .00 |
| $C_5$ | .02 |
| % CO Conversion | .4 |
| $C_2=/C_2$ | .29 |
| $C_3=/C_3$ | 2.14 |
| $C_2$-$C_6/C_1$ | .17 |

TABLE 7

Mo/Pd on WPC
Activity (Rate of formation-micromoles per sec per gm metal)
Catalyst 20% Mo + 6% Pd on WPC
(Press. = 4 atm; CO:$H_2$::1:1; GHSV = 336)

| | Temp. °C. | |
| --- | --- | --- |
| | 180° C. | 200° C. |
| Hydrocarbon Product Components | | |
| $C_1$ | 5.62 | 9.90 |
| $C_2=$ | .08 | .08 |
| $C_2$ | .45 | .84 |
| $C_3=$ | .16 | .23 |
| $C_3$ | .09 | .21 |
| $C_4$ iso | .02 | .00 |
| $C_4=$ | .03 | .03 |
| $C_4$ | .08 | .07 |
| $C_5=$ | .02 | — |
| $C_5$ | .01 | .05 |
| $C_6$ | .02 | .00 |
| % CO Conversion | 1.2 | 2.0 |
| $C_2=/C_2$ | .17 | .10 |
| $C_3=/C_3$ | 1.88 | 1.09 |
| $C_2$-$C_6/C_1$ | .17 | .15 |

The test in Example 9 demonstrates the ability of the bimetallic catalyst to have significant catalytic activity at surprisingly low temperature. Olefin to parafin product ratios are generally higher as the operating temperature is reduced, and the bimetallic catalysts can produce significant yields at very low temperatures.

We claim:

1. Catalyst particles comprising catalytic molybdenum and a second metal selected from rhodium and palladium on particulate carbon which has a pore size distribution curve characterized by a single sharp peak at a pore radius above 10 Å, surface area greater than 100 square meters per gram, pore volume greater than 0.2 cc/g, average pore radius of at least 25 Å and compacted bulk density in the range from about 0.3 to about 0.8 g/cc.

2. A method of making catalyst particles which comprises depositing Mo(CO)$_6$ on particulate carbon which has a pore size distribution curve characterized by a single sharp peak at a pore radius above 10 Å, surface area greater than 100 square meters per gram, pore volume greater than 0.2 cc/g, average pore radius of at least 25 Å and compacted bulk density in the range from about 0.3 to about 0.8 g/cc, and heating to decompose and reduce the molybdenum compound.

3. A method defined by claim 2 wherein Mo(CO)$_6$ is deposited by vapor deposition on the carbon support.

4. A method defined by claim 2 wherein Mo(CO)$_6$ is deposited by impregnating the carbon support with a solution of Mo(CO)$_6$ and evaporating the solvent.

* * * * *